(12) United States Patent
Lebreton et al.

(10) Patent No.: US 9,896,478 B2
(45) Date of Patent: Feb. 20, 2018

(54) ANTIBODY PURIFICATION BY CATION EXCHANGE CHROMATOGRAPHY

(71) Applicant: Genentech, Inc., South San Francisco, CA (US)

(72) Inventors: Benedicte Andree Lebreton, San Francisco, CA (US); Deborah Ann O'Connor, San Carlos, CA (US); Aurelia Safta, Walnut Creek, CA (US); Mandakini Sharma, Sunnyvale, CA (US)

(73) Assignee: GENENTECH, INC., South San Francisco, CA (US)

( * ) Notice: Subject to any disclaimer, the term of this patent is extended or adjusted under 35 U.S.C. 154(b) by 315 days.

(21) Appl. No.: 14/531,880

(22) Filed: Nov. 3, 2014

(65) Prior Publication Data

US 2015/0056196 A1    Feb. 26, 2015

Related U.S. Application Data

(63) Continuation of application No. 12/260,623, filed on Oct. 29, 2008, now abandoned.

(60) Provisional application No. 60/983,825, filed on Oct. 30, 2007.

(51) Int. Cl.
| | | |
|---|---|---|
| *C07K 1/18* | (2006.01) | |
| *C07K 16/06* | (2006.01) | |
| *C07K 16/22* | (2006.01) | |
| *C07K 16/28* | (2006.01) | |
| *C07K 1/36* | (2006.01) | |

(52) U.S. Cl.
CPC ............. *C07K 1/18* (2013.01); *C07K 1/36* (2013.01); *C07K 16/065* (2013.01); *C07K 16/22* (2013.01); *C07K 16/2887* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,753,894 A | 6/1988 | Frankel et al. |
| 4,966,851 A | 10/1990 | Durance et al. |
| 5,110,913 A | 5/1992 | Coan et al. |
| 5,112,951 A | 5/1992 | Beidler et al. |
| 5,115,101 A | 5/1992 | Bloom et al. |
| 5,118,796 A | 6/1992 | Prior et al. |
| 5,169,774 A | 12/1992 | Frankel et al. |
| 5,196,323 A | 3/1993 | Bodo et al. |
| 5,256,769 A | 10/1993 | Kato et al. |
| 5,279,823 A | 1/1994 | Frenz et al. |
| 5,429,746 A | 7/1995 | Shadle et al. |
| 5,451,662 A | 9/1995 | Naveh et al. |
| 5,525,338 A | 6/1996 | Goldenberg |
| 5,677,171 A | 10/1997 | Hudziak et al. |
| 5,736,137 A | 4/1998 | Anderson et al. |
| 6,005,081 A | 12/1999 | Burton et al. |
| 6,054,561 A | 4/2000 | Ring |
| 6,127,526 A | 10/2000 | Blank |
| 6,267,958 B1 | 7/2001 | Andya et al. |
| 6,333,398 B1 | 12/2001 | Blank |
| 6,339,142 B1 | 1/2002 | Basey et al. |
| 6,417,335 B1 | 7/2002 | Basey et al. |
| 6,417,355 B1 | 7/2002 | Chapman et al. |
| 6,489,447 B1 | 12/2002 | Basey et al. |
| 6,797,814 B2 | 9/2004 | Blank |
| 7,060,269 B1 | 6/2006 | Baca et al. |
| 7,074,404 B2 | 7/2006 | Basey et al. |
| 7,169,901 B2 | 1/2007 | Baca et al. |
| 2004/0082047 A1 | 4/2004 | Emery et al. |
| 2005/0063972 A1 | 3/2005 | Basey et al. |
| 2006/0182740 A1 | 8/2006 | Yang et al. |
| 2006/0257972 A1 * | 11/2006 | Ishihara ............... C07K 16/065 435/69.1 |
| 2009/0148435 A1 | 6/2009 | Lebreton et al. |

FOREIGN PATENT DOCUMENTS

| | | | | |
|---|---|---|---|---|
| CH | WO 2008025748 A1 * | 3/2008 | ............... | C07K 1/18 |
| CL | 800-1983 | 11/1983 | | |
| CN | 1299370 A | 6/2001 | | |
| EP | 0 110 044 A1 | 6/1984 | | |
| EP | 0 33 574 B1 | 9/1989 | | |
| EP | 0 467 466 A1 | 1/1992 | | |
| EP | 0 669 836 B1 | 7/1996 | | |
| EP | 0 556 083 B1 | 8/1996 | | |
| EP | 0 460 426 B1 | 9/1997 | | |
| EP | 1 075 488 B1 | 5/2003 | | |
| EP | 0 971 959 B1 | 12/2005 | | |
| JP | 8-503468 | 4/1996 | | |
| JP | 2001-509817 | 7/2001 | | |
| JP | 2002-513800 | 5/2002 | | |
| WO | 89/05157 | 6/1989 | | |

(Continued)

OTHER PUBLICATIONS

Certified U.S. Appl. No. 60/983,825, filed Oct. 30, 2007.
Communication from Examining Division dated Sep. 4, 2012 in EP Appln. No. 08844379.1.
Opposition file by Glaxo Group Limited in EP2215117 on Sep. 29, 2015.
Opposition filed by Mr. Ross Walker in EP2215117 on Sep. 29, 2015.
Patentee's Response to Examining Division dated Dec. 3, 2010 in EP Appln. No. 08844379.1.
Rituximab Label1997.

(Continued)

*Primary Examiner* — Daniel E Kolker
*Assistant Examiner* — James L Rogers
(74) *Attorney, Agent, or Firm* — Morrison & Foerster LLP

(57) ABSTRACT

A method for purifying an antibody by cation exchange chromatography is described in which a high pH wash step is used to remove of contaminants prior to eluting the desired antibody using an elution buffer with increased conductivity.

14 Claims, 5 Drawing Sheets

(56) References Cited

FOREIGN PATENT DOCUMENTS

| WO | 92/22653 | 12/1992 |
| WO | 93/06217 | 4/1993 |
| WO | 94/11026 | 5/1994 |
| WO | 95/22389 | 8/1995 |
| WO | 96/33208 | 10/1996 |
| WO | 96/40883 | 12/1996 |
| WO | 98/45331 | 10/1998 |
| WO | 99/57134 | 11/1999 |
| WO | 99/62936 | 12/1999 |
| WO | WO-1999/064462 A1 | 12/1999 |
| WO | 02/096457 | 12/2002 |
| WO | 2004/001007 | 12/2003 |
| WO | 2004/024866 A2 | 3/2004 |
| WO | 2004/024866 A3 | 3/2004 |
| WO | WO-2004/054615 A1 | 7/2004 |
| WO | WO-2004/060920 A1 | 7/2004 |
| WO | WO-2005/032130 A1 | 4/2005 |
| WO | 2005/066139 | 7/2005 |
| WO | 2005/115453 A2 | 12/2005 |
| WO | 2006/069403 A2 | 6/2006 |
| WO | WO-2006/099308 A2 | 9/2006 |
| WO | WO-2006/138737 A2 | 12/2006 |
| WO | WO-2007/028154 A2 | 3/2007 |
| WO | 2007/108955 | 9/2007 |
| WO | 2007/117490 A2 | 10/2007 |
| WO | 2008/028154 A2 | 3/2008 |

OTHER PUBLICATIONS

Amersham Biosciences Ion Exchange Chromatography & Chromatofocusing "Principles and Methods" Handbook Edition AA edition, ( 2004).

Coppola et al., "High-performance liquid chromatography of amino acids, peptides and proteins; XCIII alpha Comparison of methods for the purification of mouse monoclonal immunoglobulin M autoantibodies" Journal of Chromatography 476:269-290 ( 1989).

Ishihara et al., "Accelerated purification process development of monoclonal antibodies for shortening time to clinic Design and case study of chromatography processes" Journal of Chromatography A 1176:149-156 ( 2007).

(Experimental data submitted w/Genentech's response filed Jun. 17, 2016 to Oppositions of EP No. 2215117).

Presta et al., "Humanization of an Anti-Vascular Endothelial Growth Factor Monoclonal Antibody for the Therapy of Solid Tumors and Other Disorders" Cancer Research 57:4593-4599 (Oct. 15, 1997).

Tosoh Bioscience GMBH, "Use of Hydrophobic Interaction Chromatography with a Non-Salt Buffer System for Improving Process Economics in Purification of Monclonal Antibodies" Abstract Waterside Conference on Monoclonal and Recombinant Antibodies, Miami, Florida, USA, (2000).

Tosoh Bioscience GmbH, "Use of Hydrophobic Interaction Chromatography with a Non-salt Buffer System for Improving Process Economics in Purification of Monoclonal Antibodies" Other Waterside Conference on Monoclonal and Recombinant Antibodies, Miami, FL, (2000).

Adachi et al., "Ion-exchange high-performance liquid chromatographic separation of protein variants and isoforms on MCI GEL ProtEx stationary phases" Journal of Chromatography. A. 763(1-2):57-63 (Feb. 28, 1997).

Barnthouse et al., "Cation-exchange displacement chromatography for the purification of recombinant protein therapeutics from variants" J Biotechnol. 66(2-3):125-36 (Dec. 11, 1998).

Blank et al., "Expanded bed adsorption in the purification of monoclonal antibodies: a comparison of process alternatives" Bioseparation 10(1-3):65-71 (2001).

International Search Report dated Apr. 1, 2009, received in corresponding PCT Application No. PCT/US2008/081516.

Written Opinion dated Apr. 1, 2009, received in corresponding PCT Application No. PCT/US2008/081516.

Denton et al., "Direct isolation of monoclonal antibodies from tissue culture supernatant using the cation-exchange cellulose Express-Ion S" Journal of Chromatography A 908:223-234 ( 2001).

Faude et al., "Fast determination of conditions for maximum dynamic capacity in cation-exchange chromatography of human monoclonal antibodies" Journal of Chromatography A 1161:29-35 ( 2007).

Ferrara, N. et al., "Discovery and Development of Bevacizumab, an Anti-VEGF Antibody for Treating Cancer" Nature Reviews—Drug Discovery 3:391-400 (May 2004).

Follman et al. et al., "Factorial screening of antibody purification processes using three chromatography steps without protein A" J CHROMATOGR 1024(1-2):79-85 ( 2004).

Gagnon, P., "Ion Exchange Chromatography" Purification Tools for Monoclonal Antibodies, Tucson:Validated Biosystems, Inc., Chapter 4, pp. 57-86 (1996).

Golay et al., "Rituximab-mediated antibody-dependent celluar cytotoxicity against neoplastic B Cells is Stimulated Strongly by Interleukin-2" Haematologica/Journal of Hematology 88(09):1002-1012 (Sep. 2003).

Graf et al., "Ion exchange resins for the purification of monoclonal antibodies from animal cell culture" Bioseparation 4(1):7-20 (Feb. 1994).

Harris and Angal Protein Purification Applications—A Practical Approach pp. 151-156 (1995).

Ishihara et al., "Optimization of elution salt concentration in stepwise elution of protein chromatography using linear gradient elution data reducing residual protein a by cation-exchange chromatography in monoclonal antibody purification" Journal of Chromatography 1114(1):97-101 ( 2006).

Ishihara et al., "Optimization of monoclonal antibody purification by ion-exchange chromatography" Journal of Chromatography 1069(1):99-106 ( 2005).

Iyer et al., "Considerations During Development of a Protein A-Based Antibody Purification Process" BioPharm 15(1):14-16, 18, 20, 53 (Jan. 2002).

Mhatre et al., "Purification of antibody Fab fragments by cation-exchange chromatography and pH gradient elution" Journal of Chromatography A 707(2):225-231 (Jul. 21, 1995).

Mordenti et al., "Efficacy and Concentration-Response of Murine Anti-VEGF Monoclonal Antibody in Tumor-Bearing Mice and Extrapolation to Humans" Toxicologic Pathology 27(1):14-21 ( 1999).

Nagira et al., "Effects of organic pH buffers on a cell growth and an antibody production of human-human hybridom HB4C5 cells in a serum-free culture" Cytotechnology 17:117-125 ( 1995).

Necina et al., "Capture of human monoclonal antibodies from cellc ulture supernatant by ion exchange media exhibiting high charge density" Biotechnol Bioeng 60(6):689-698 (Dec. 20, 1998).

Neidhardt et al., "Rapid, two-step purification process for the preparation of pyrogen-free murine immunoglobulin G\{cube root}\subscript:1\\\ monoclonal antibodies" Journal of Chromatography 590(2):255-261 (1992).

Rad F. H. et al., "VEGF kinoid vaccine, a therapeutic approach against tumor angiogenesis and metastases" PNAS 104(8):2837-2842 (Feb. 2007).

Sofer et al. Handbook of Process Chromatography: A Guide to Optimization, Scale-up, and Validation, San Diego:Academic Press pp. 65-81 (1997).

Stein et al., "Cation Exchange Chromatography in Antibody Purification: pH Screening for Optimised Binding and HCP Removal" Journal of Chromatography B, 848, (Mar. 12, 2007), pp. 151-158.

Stein et al., "Cation exchange chromatography in antibody purification: pH screening for optimized binding and HCP removal" Journal of Chromatography 848(1):151-158 ( 2007).

Tishchenko et al., "Effect of salt concentration gradient on separation of different types of specific immunoglobulins by ion-exchange chromatography on DEAE cellulose" Journal of Chromatography B 706(1):157-166 (Feb. 27, 1998).

Zhang et al., "Q Membrane Chromatography Application for Human Antibody Purification Process" (Poster presented at BioProduction, Oct. 26-27. Munich, Germany, 2004 (1page)).

(56) References Cited

OTHER PUBLICATIONS

Zhou et al., "pH-conductivity hybrid gradient cation-exchange chromatography for process-scale monoclonal antibody purification" Journal of Chromatography 1175:69-80 ( 2007).
Cromwell, M.E.M. (2006, e-pub. Sep. 15, 2006). "Protein Aggregation and Bioprocessing", *The AAPS Journal* 8(3) Article 66:E572-E579.
Farhner, R.L. et al. (Jul. 2001). "Industrial Purification of Pharmaceutical Antibodies: Development, Operation, and Validation of Chromatography Processes", *Biotechnology and Genetic Engineering Reviews* 18:301-327.
Interlocutory Decision in Opposition Proceedings mailed Jun. 28, 2017, for EP Patent Application No. 08844379.1, by European Patent Office Opposition Division, 2 pages.
Summons to Attend Oral Proceedings mailed on Oct. 13, 2016 for EP Patent Application No. 08844379.1, by European Patent Office Opposition Division, 24 pages.
Low, D. et al. (Mar. 15, 2007, E-pub. Nov. 28, 2006). "Future of Antibody Purification", *J Chromatogr B Analyt Biomed Life Sci.* 848(1):48-63.
Lebedev L.R. et al. (2001). "A Method for Purifying Tumor Necrosis Factor Antagonists and a Study of Some of Their Properties", *Biotechnology*, No. 6, pp. 14-18. (Russian) (English Translation).
Maintenance of the Patent with the Documents Specified in the Final Decision, Oct. 10, 2017, EPO Form 2335, 1 page.
Moore, J.M.R. et al. (1999, e-pub. Sep. 28, 1999). "Kinetics and Thermodynamics of Dimer Formation and Dissociation for a Recombinant Humanized Monoclonal Antibody to Vascular Endothelial Growth Factor", *Biochemistry*, 38(42):13960-13967.
Opposition document filed by Glaxo Group Limited on Feb. 20, 2017, in EP Patent Application No. 08844379.1, 3 pages.
Opposition document filed by Ross Walker, et al. on Apr. 13, 2017, in EP Patent Application No. 08844379.1, 3 pages.
Patentee's Submission in Opposition Proceedings dated May 25, 2017, in EP Patent Application No. 08844379.1, 10 pages.
Patentee's Response Letter and Claim Requests dated Jun. 17, 2016, in EP Patent Application. No. 08844379.1, 75 pages.
WHO (2000). "International Nonproprietary Names for Pharmaceutical Substances, Proposed International Nonproprietary Names: List 83", *Drug Information* 14(2):107-143.

\* cited by examiner

Fig. 1A – Rituximab Heavy Chain

```
       |  +1      FR1                              10                  15
       | Gln Val Gln Leu Gln Gln Pro Gly Ala Glu Leu Val Lys Pro Gly Ala
Ser    |

20                  25                  30| 31    CDR1       35|
36
 Val Lys Met Ser Cys Lys Ala Ser Gly Tyr Thr Phe Thr|Ser Tyr Asn Met His|
Trp

40   FR2            45                  49| 50     52 52A   53
54
 Val Lys Gln Thr Pro Gly Arg Gly Leu Glu Trp Ile Gly|Ala Ile Tyr Pro Gly
Asn

55        CDR2       60                      65| 66   FR3           70
 Gly Asp Thr Ser Tyr Asn Gln Lys Phe Lys Gly| Lys Ala Thr Leu Thr Ala Asp
Lys 75                  80     82 82A 82B 82C 83        85
 Ser Ser Ser Thr Ala Tyr Met Gln Leu Ser Ser Leu Thr Ser Glu Asp Ser Ala
Val 90                  94| 95   CDR3        100 100A 100B 100C 100D 101 102 103
 Tyr Tyr Cys Ala Arg|Ser Thr Tyr Tyr Gly Gly Asp Trp Tyr Phe Asn Val|Trp
Gly

105  FR4            110           113|114                     120
 Ala Gly Thr Thr Val Thr Val Ser Ala|Ala Ser Thr Lys Gly Pro Ser Val Phe
Pro
```

Human Gamma 1 Constant

```
130 133                         140
 Leu Ala Pro Ser Ser Lys Ser Thr Ser Gly Gly Thr Ala Ala Leu Gly Cys Leu
Val 150             154 156 157 162
 Lys Asp Tyr Phe Pro Glu Pro Val Thr Val Ser Trp Asn Ser Gly Ala Leu Thr Ser 169 171                             180 182
 Gly Val His Thr Phe Pro Ala Val Leu Gln Ser Ser Gly Leu Tyr Ser Leu Ser Ser 190                               200 203 205                   210
 Val Val Thr Val Pro Ser Ser Ser Leu Gly Thr Gln Thr Tyr Ile Cys Asn Val Asn 220    222| 225                230 232 235
 His Lys Pro Ser Asn Thr Lys Val Asp Lys Lys|Ala Glu Pro Lys Ser Cys Asp Lys 240         243|244                250
 Thr His Thr Cys Pro Pro Cys Pro|Ala Pro Glu Leu Leu Gly Gly Pro Ser Val Phe
```

```
                260                                    270
Leu Phe Pro Pro Lys Pro Lys Asp Thr Leu Met Ile Ser Arg Thr Pro Glu Val Thr
```

Human Gamma 1 Constant – continued

```
     280                                          290     292
Cys Val Val Val Asp Val Ser His Glu Asp Pro Glu Val Lys Phe Asn Trp Tyr Val 295 296 299 300                                         310              314 317
Asp Gly Val Glu Val His Asn Ala Lys Thr Lys Pro Arg Glu Glu Gln Tyr Asn Ser 320                                    330
Thr Tyr Arg Val Val Ser Val Leu Thr Val Leu His Gln Asp Trp Leu Asn Gly Lys 340                                          350              355
Glu Tyr Lys Cys Lys Val Ser Asn Lys Ala Leu Pro Ala Pro Ile Glu Lys Thr Ile 357           360 361 363                         370
Ser Lys Ala Lys Gly Gln Pro Arg Glu Pro Gln Val Tyr Thr Leu Pro Pro Ser Arg 378 381                                 390
Asp Glu Leu Thr Lys Asn Gln Val Ser Leu Thr Cys Leu Val Lys Gly Phe Tyr
Pro 400     402 405         408 410 413                         420
Ser Asp Ile Ala Val Glu Trp Glu Ser Asn Gly Gln Pro Glu Asn Asn Tyr Lys
Thr 428 430 433                         440
Thr Pro Pro Val Leu Asp Ser Asp Gly Ser Phe Phe Leu Tyr Ser Lys Leu Thr
Val 450                                         460
Asp Lys Ser Arg Trp Gln Gln Gly Asn Val Phe Ser Cys Ser Val Met His Glu
Ala 470                             478    Amino
Acid # (Kabat)
Leu His Asn His Tyr Thr Gln Lys Ser Leu Ser Leu Ser Pro Gly Lys TER
```

Fig. 1A (continued)

Fig. 1B - Rituximab Light Chain

```
      +1        FR1                                        10
     Gln Ile Val Leu Ser Gln Ser Pro Ala Ile Leu Ser Ala Ser 20              23  24      CDR1      27/ 29  30                  34
Pro Gly Glu Lys Val Thr Met Thr Cys Arg Ala Ser Ser Ser Val Ser Tyr Ile His

35        FR2              40                  45              49  50      CDR2
Trp Phe Gln Gln Lys Pro Gly Ser Ser Pro Lys Pro Trp Ile Tyr Ala Thr Ser Asn 55  56  57              60          FR3       65                       70
Leu Ala Ser Gly Val Pro Val Arg Phe Ser Gly Ser Gly Ser Gly Thr Ser Tyr Ser 75                      80                  85              88  89  90
Leu Thr Ile Ser Arg Val Glu Ala Glu Asp Ala Ala Thr Tyr Tyr Cys Gln Gln Trp

CDR3  95          97  98      100   FR4                 105         107 108         110
Thr Ser Asn Pro Pro Thr Phe Gly Gly Gly Thr Lys Leu Glu Ile Lys Arg Thr Val

120
Ala Ala Pro Ser Val Phe Ile Phe Pro Pro Ser Asp Glu Gln Leu Lys Ser Gly Thr
```

Human Kappa Constant

```
130                                      140
Ala Ser Val Val Cys Leu Leu Asn Asn Phe Tyr Pro Arg Glu Ala Lys Val Gln Trp 150                                  160
Lys Val Asp Asn Ala Leu Gln Ser Gly Asn Ser Gln Glu Ser Val Thr Glu Gln Asp 170                                  180
Ser Lys Asp Ser Thr Tyr Ser Leu Ser Ser Thr Leu Thr Leu Ser Lys Ala Asp Tyr 190                                  200
Glu Lys His Lys Val Tyr Ala Cys Glu Val Thr His Gln Gly Leu Ser Ser Pro Val 210             214              Amino Acid # (kabat)
Thr Lys Ser Phe Asn Arg Gly Glu Cys TER
```

Fig. 2A - Bevacizumab Heavy Chain

EVQLVESGGGLVQPGGSLRLSCAAS<u>GYTFTNYGMN</u>WVRQAPGK
GLEWVG<u>WINTYTGEPTYAADFKR</u>RFTFSLDTSKSTAYLQMNSLR
AEDTAVYYCAKY<u>PHYYGSSHWYFDV</u>WGQGTLVTVSS ‖ ASTKGP
SVFPLAPSSKSTSGGTAALGCLVKDYFPEPVTVSWNSGALTSGVH
TFPAVLQSSGLYSLSSVVTVPSSSLGTQTYICNVNHKPSNTKVDKK
VEPKSCDKTHTCPPCPAPELLGGPSVFLFPPKPKDTLMISRTPEVTC
VVVDVSHEDPEVKFNWYVDGVEVHNAKTKPREEQYNSTYRVVS
VLTVLHQDWLNGKEYKCKVSNKALPAPIEKTISKAKGQPREPQV
YTLPPSREEMTKNQVSLTCLVKGFYPSDIAVEWESNGQPENNYKT
TPPVLDSDGSFFLYSKLTVDKSRWQQGNVFSCSVMHEALHNHYT
QKSLSLSPGK

Fig. 2B - Bevacizumab Light Chain

DIQMTQSPSSLSASVGDRVTITC<u>SASQDISNYLN</u>WYQQKPGKAPK
VLIY<u>FTSSLHS</u>GVPSRFSGSGSGTDFTLTISSLQPEDFATYYC<u>QQYS
TVPWT</u>FGQGTKVEIKR ‖ TVAAPSVFIFPPSDEQLKSGTASVVCLLN
NFYPREAKVQWKVDNALQSGNSQESVTEQDSKDSTYSLSSTLTLS
KADYEKHKVYACEVTHQGLSSPVTKSFNRGEC

FIG. 3 – Host Cell Proteins Removal for Rituximab Processes
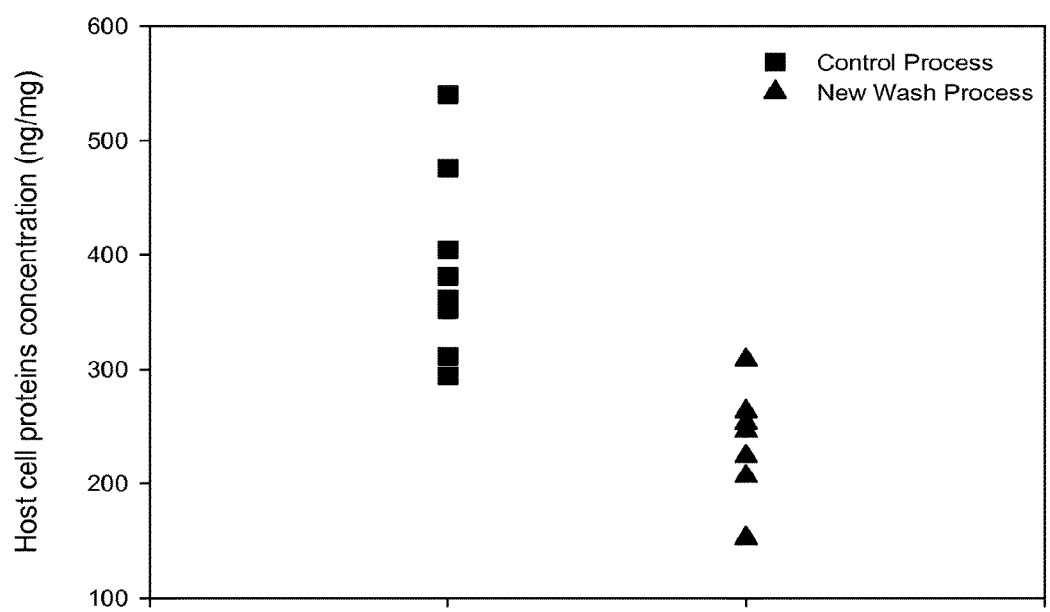

```
                        SEQUENCE LISTING

<160> NUMBER OF SEQ ID NOS: 20

<210> SEQ ID NO 1
<211> LENGTH: 432
<212> TYPE: PRT
<213> ORGANISM: Artificial sequence
<220> FEATURE:
<223> OTHER INFORMATION: sequence is synthesized

<400> SEQUENCE: 1

Gln Val Gln Leu Gln Gln Pro Gly Ala Glu Leu Val Lys Pro Gly
  1               5                  10                  15

Ala Ser Val Lys Met Ser Cys Lys Ala Ser Gly Tyr Thr Phe Thr
                 20                  25                  30

Ser Tyr Asn Met His Trp Val Lys Gln Thr Pro Gly Arg Gly Leu
                 35                  40                  45

Glu Trp Ile Gly Ala Ile Tyr Pro Gly Asn Gly Asp Thr Ser Tyr
                 50                  55                  60

Asn Gln Lys Phe Lys Gly Lys Ala Thr Leu Thr Ala Asp Lys Ser
                 65                  70                  75

Ser Ser Thr Ala Tyr Met Gln Leu Ser Ser Leu Thr Ser Glu Asp
                 80                  85                  90

Ser Ala Val Tyr Tyr Cys Ala Arg Ser Thr Tyr Tyr Gly Gly Asp
                 95                 100                 105

Trp Tyr Phe Asn Val Trp Gly Ala Gly Thr Thr Val Thr Val Ser
                110                 115                 120

Ala Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210
```

Ser Asn Thr Lys Val Asp Lys Lys Ala Glu Pro Lys Ser Cys Asp
            215                 220                 225

Lys Thr His Thr Cys Pro Pro Cys Pro Ala Pro Glu Leu Leu Gly
            230                 235                 240

Gly Pro Ser Val Phe Leu Phe Pro Pro Lys Pro Lys Asp Thr Leu
            245                 250                 255

Met Ile Ser Arg Thr Pro Glu Val Thr Asp Gly Val Glu Val His
            260                 265                 270

Asn Ala Lys Thr Lys Pro Arg Glu Glu Gln Tyr Asn Ser Thr Tyr
            275                 280                 285

Arg Val Val Ser Val Leu Thr Val Leu His Gln Asp Trp Leu Asn
            290                 295                 300

Gly Lys Glu Tyr Lys Cys Lys Val Ser Asn Lys Ala Leu Pro Ala
            305                 310                 315

Pro Ile Glu Lys Thr Ile Ser Lys Ala Lys Gly Gln Pro Arg Glu
            320                 325                 330

Pro Gln Val Tyr Thr Leu Pro Pro Ser Arg Asp Glu Leu Thr Lys
            335                 340                 345

Asn Gln Val Ser Leu Thr Cys Leu Val Lys Gly Phe Tyr Pro Ser
            350                 355                 360

Asp Ile Ala Val Glu Trp Glu Ser Asn Gly Gln Pro Glu Asn Asn
            365                 370                 375

Tyr Lys Thr Thr Pro Pro Val Leu Asp Ser Asp Gly Ser Phe Phe
            380                 385                 390

Leu Tyr Ser Lys Leu Thr Val Asp Lys Ser Arg Trp Gln Gln Gly
            395                 400                 405

Asn Val Phe Ser Cys Ser Val Met His Glu Ala Leu His Asn His
            410                 415                 420

Tyr Thr Gln Lys Ser Leu Ser Leu Ser Pro Gly Lys
            425                 430

<210> SEQ ID NO 2
<211> LENGTH: 213
<212> TYPE: PRT
<213> ORGANISM: Artificial sequence
<220> FEATURE:
<223> OTHER INFORMATION: sequence is synthesized

<400> SEQUENCE: 2

Gln Ile Val Leu Ser Gln Ser Pro Ala Ile Leu Ser Ala Ser Pro
  1               5                  10                  15

Gly Glu Lys Val Thr Met Thr Cys Arg Ala Ser Ser Ser Val Ser
             20                  25                  30

Tyr Ile His Trp Phe Gln Gln Lys Pro Gly Ser Ser Pro Lys Pro
            35                  40                  45

Trp Ile Tyr Ala Thr Ser Asn Leu Ala Ser Gly Val Pro Val Arg
            50                  55                  60

Phe Ser Gly Ser Gly Ser Gly Thr Ser Tyr Ser Leu Thr Ile Ser
            65                  70                  75

Arg Val Glu Ala Glu Asp Ala Ala Thr Tyr Tyr Cys Gln Gln Trp
            80                  85                  90

Thr Ser Asn Pro Pro Thr Phe Gly Gly Gly Thr Lys Leu Glu Ile
            95                  100                 105

Lys Arg Thr Val Ala Ala Pro Ser Val Phe Ile Phe Pro Pro Ser
            110                 115                 120

-continued

Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 3
<211> LENGTH: 121
<212> TYPE: PRT
<213> ORGANISM: Artificial sequence
<220> FEATURE:
<223> OTHER INFORMATION: sequence is synthesized

<400> SEQUENCE: 3

Gln Val Gln Leu Gln Gln Pro Gly Ala Glu Leu Val Lys Pro Gly
  1               5                  10                  15

Ala Ser Val Lys Met Ser Cys Lys Ala Ser Gly Tyr Thr Phe Thr
             20                  25                  30

Ser Tyr Asn Met His Trp Val Lys Gln Thr Pro Gly Arg Gly Leu
             35                  40                  45

Glu Trp Ile Gly Ala Ile Tyr Pro Gly Asn Gly Asp Thr Ser Tyr
             50                  55                  60

Asn Gln Lys Phe Lys Gly Lys Ala Thr Leu Thr Ala Asp Lys Ser
             65                  70                  75

Ser Ser Thr Ala Tyr Met Gln Leu Ser Ser Leu Thr Ser Glu Asp
             80                  85                  90

Ser Ala Val Tyr Tyr Cys Ala Arg Ser Thr Tyr Tyr Gly Gly Asp
             95                 100                 105

Trp Tyr Phe Asn Val Trp Gly Ala Gly Thr Thr Val Thr Val Ser
            110                 115                 120

Ala

<210> SEQ ID NO 4
<211> LENGTH: 106
<212> TYPE: PRT
<213> ORGANISM: Artificial sequence
<220> FEATURE:
<223> OTHER INFORMATION: sequence is synthesized

<400> SEQUENCE: 4

Gln Ile Val Leu Ser Gln Ser Pro Ala Ile Leu Ser Ala Ser Pro
  1               5                  10                  15

Gly Glu Lys Val Thr Met Thr Cys Arg Ala Ser Ser Ser Val Ser
             20                  25                  30

Tyr Ile His Trp Phe Gln Gln Lys Pro Gly Ser Ser Pro Lys Pro
             35                  40                  45

Trp Ile Tyr Ala Thr Ser Asn Leu Ala Ser Gly Val Pro Val Arg
             50                  55                  60

```
Phe Ser Gly Ser Gly Ser Gly Thr Ser Tyr Ser Leu Thr Ile Ser
             65                  70                  75

Arg Val Glu Ala Glu Asp Ala Ala Thr Tyr Tyr Cys Gln Gln Trp
         80                  85                  90

Thr Ser Asn Pro Pro Thr Phe Gly Gly Gly Thr Lys Leu Glu Ile
             95                 100                 105

Lys

<210> SEQ ID NO 5
<211> LENGTH: 5
<212> TYPE: PRT
<213> ORGANISM: Artificial sequence
<220> FEATURE:
<223> OTHER INFORMATION: sequence is synthesized

<400> SEQUENCE: 5

Ser Tyr Asn Met His
                 5

<210> SEQ ID NO 6
<211> LENGTH: 17
<212> TYPE: PRT
<213> ORGANISM: Artificial sequence
<220> FEATURE:
<223> OTHER INFORMATION: sequence is synthesized

<400> SEQUENCE: 6

Ala Ile Tyr Pro Gly Asn Gly Asp Thr Ser Tyr Asn Gln Lys Phe
 1               5                  10                  15

Lys Gly

<210> SEQ ID NO 7
<211> LENGTH: 12
<212> TYPE: PRT
<213> ORGANISM: Artificial sequence
<220> FEATURE:
<223> OTHER INFORMATION: sequence is synthesized

<400> SEQUENCE: 7

Ser Thr Tyr Tyr Gly Gly Asp Trp Tyr Phe Asn Val
                 5                  10

<210> SEQ ID NO 8
<211> LENGTH: 10
<212> TYPE: PRT
<213> ORGANISM: Artificial sequence
<220> FEATURE:
<223> OTHER INFORMATION: sequence is synthesized

<400> SEQUENCE: 8

Arg Ala Ser Ser Ser Val Ser Tyr Ile His
                 5                  10

<210> SEQ ID NO 9
<211> LENGTH: 7
<212> TYPE: PRT
<213> ORGANISM: Artificial sequence
<220> FEATURE:
<223> OTHER INFORMATION: sequence is synthesized

<400> SEQUENCE: 9

Ala Thr Ser Asn Leu Ala Ser
                 5
```

```
<210> SEQ ID NO 10
<211> LENGTH: 9
<212> TYPE: PRT
<213> ORGANISM: Artificial sequence
<220> FEATURE:
<223> OTHER INFORMATION: sequence is synthesized

<400> SEQUENCE: 10

Gln Gln Trp Thr Ser Asn Pro Pro Thr
                 5

<210> SEQ ID NO 11
<211> LENGTH: 453
<212> TYPE: PRT
<213> ORGANISM: Artificial sequence
<220> FEATURE:
<223> OTHER INFORMATION: sequence is synthesized

<400> SEQUENCE: 11

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Asn Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Gly Ser
                 95                 100                 105

Ser His Trp Tyr Phe Asp Val Trp Gly Gln Gly Thr Leu Val Thr
                110                 115                 120

Val Ser Ser Ala Ser Thr Lys Gly Pro Ser Val Phe Pro Leu Ala
                125                 130                 135

Pro Ser Ser Lys Ser Thr Ser Gly Gly Thr Ala Ala Leu Gly Cys
                140                 145                 150

Leu Val Lys Asp Tyr Phe Pro Glu Pro Val Thr Val Ser Trp Asn
                155                 160                 165

Ser Gly Ala Leu Thr Ser Gly Val His Thr Phe Pro Ala Val Leu
                170                 175                 180

Gln Ser Ser Gly Leu Tyr Ser Leu Ser Ser Val Val Thr Val Pro
                185                 190                 195

Ser Ser Ser Leu Gly Thr Gln Thr Tyr Ile Cys Asn Val Asn His
                200                 205                 210

Lys Pro Ser Asn Thr Lys Val Asp Lys Lys Val Glu Pro Lys Ser
                215                 220                 225

Cys Asp Lys Thr His Thr Cys Pro Pro Cys Pro Ala Pro Glu Leu
                230                 235                 240

Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val
                275                 280                 285
```

```
Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu
        305                 310                 315

His Gln Asp Trp Leu Asn Gly Lys Glu Tyr Lys Cys Lys Val Ser
    320                 325                 330

Asn Lys Ala Leu Pro Ala Pro Ile Glu Lys Thr Ile Ser Lys Ala
335                 340                 345

Lys Gly Gln Pro Arg Glu Pro Gln Val Tyr Thr Leu Pro Pro Ser
            350                 355                 360

Arg Glu Glu Met Thr Lys Asn Gln Val Ser Leu Thr Cys Leu Val
        365                 370                 375

Lys Gly Phe Tyr Pro Ser Asp Ile Ala Val Glu Trp Glu Ser Asn
    380                 385                 390

Gly Gln Pro Glu Asn Asn Tyr Lys Thr Thr Pro Pro Val Leu Asp
395                 400                 405

Ser Asp Gly Ser Phe Phe Leu Tyr Ser Lys Leu Thr Val Asp Lys
            410                 415                 420

Ser Arg Trp Gln Gln Gly Asn Val Phe Ser Cys Ser Val Met His
        425                 430                 435

Glu Ala Leu His Asn His Tyr Thr Gln Lys Ser Leu Ser Leu Ser
    440                 445                 450

Pro Gly Lys

<210> SEQ ID NO 12
<211> LENGTH: 214
<212> TYPE: PRT
<213> ORGANISM: Artificial sequence
<220> FEATURE:
<223> OTHER INFORMATION: sequence is synthesized

<400> SEQUENCE: 12

Asp Ile Gln Met Thr Gln Ser Pro Ser Ser Leu Ser Ala Ser Val
  1               5                  10                  15

Gly Asp Arg Val Thr Ile Thr Cys Ser Ala Ser Gln Asp Ile Ser
             20                  25                  30

Asn Tyr Leu Asn Trp Tyr Gln Gln Lys Pro Gly Lys Ala Pro Lys
         35                  40                  45

Val Leu Ile Tyr Phe Thr Ser Ser Leu His Ser Gly Val Pro Ser
     50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Tyr Ser Thr Val Pro Trp Thr Phe Gly Gln Gly Thr Lys Val Glu
         95                 100                 105

Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
        140                 145                 150

Asp Asn Ala Leu Gln Ser Gly Asn Ser Gln Glu Ser Val Thr Glu
    155                 160                 165
```

```
Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 13
<211> LENGTH: 123
<212> TYPE: PRT
<213> ORGANISM: Artificial sequence
<220> FEATURE:
<223> OTHER INFORMATION: sequence is synthesized

<400> SEQUENCE: 13

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Asn Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Gly Ser
                 95                 100                 105

Ser His Trp Tyr Phe Asp Val Trp Gly Gln Gly Thr Leu Val Thr
                110                 115                 120

Val Ser Ser

<210> SEQ ID NO 14
<211> LENGTH: 108
<212> TYPE: PRT
<213> ORGANISM: Artificial sequence
<220> FEATURE:
<223> OTHER INFORMATION: sequence is synthesized

<400> SEQUENCE: 14

Asp Ile Gln Met Thr Gln Ser Pro Ser Ser Leu Ser Ala Ser Val
  1               5                  10                  15

Gly Asp Arg Val Thr Ile Thr Cys Ser Ala Ser Gln Asp Ile Ser
                 20                  25                  30

Asn Tyr Leu Asn Trp Tyr Gln Gln Lys Pro Gly Lys Ala Pro Lys
                 35                  40                  45

Val Leu Ile Tyr Phe Thr Ser Ser Leu His Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Tyr Ser Thr Val Pro Trp Thr Phe Gly Gln Gly Thr Lys Val Glu
                 95                 100                 105

Ile Lys Arg
```

```
<210> SEQ ID NO 15
<211> LENGTH: 10
<212> TYPE: PRT
<213> ORGANISM: Artificial sequence
<220> FEATURE:
<223> OTHER INFORMATION: sequence is synthesized

<400> SEQUENCE: 15

Gly Tyr Thr Phe Thr Asn Tyr Gly Met Asn
                  5                  10

<210> SEQ ID NO 16
<211> LENGTH: 17
<212> TYPE: PRT
<213> ORGANISM: Artificial sequence
<220> FEATURE:
<223> OTHER INFORMATION: sequence is synthesized

<400> SEQUENCE: 16

Trp Ile Asn Thr Tyr Thr Gly Glu Pro Thr Tyr Ala Ala Asp Phe
 1               5                  10                  15

Lys Arg

<210> SEQ ID NO 17
<211> LENGTH: 13
<212> TYPE: PRT
<213> ORGANISM: Artificial sequence
<220> FEATURE:
<223> OTHER INFORMATION: sequence is synthesized

<400> SEQUENCE: 17

Pro His Tyr Tyr Gly Ser Ser His Trp Tyr Phe Asp Val
                  5                  10

<210> SEQ ID NO 18
<211> LENGTH: 11
<212> TYPE: PRT
<213> ORGANISM: Artificial sequence
<220> FEATURE:
<223> OTHER INFORMATION: sequence is synthesized

<400> SEQUENCE: 18

Ser Ala Ser Gln Asp Ile Ser Asn Tyr Leu Asn
                  5                  10

<210> SEQ ID NO 19
<211> LENGTH: 7
<212> TYPE: PRT
<213> ORGANISM: Artificial sequence
<220> FEATURE:
<223> OTHER INFORMATION: sequence is synthesized

<400> SEQUENCE: 19

Phe Thr Ser Ser Leu His Ser
                  5

<210> SEQ ID NO 20
<211> LENGTH: 9
<212> TYPE: PRT
<213> ORGANISM: Artificial sequence
<220> FEATURE:
<223> OTHER INFORMATION: sequence is synthesized

<400> SEQUENCE: 20

Gln Gln Tyr Ser Thr Val Pro Trp Thr
                  5
```

ANTIBODY PURIFICATION BY CATION EXCHANGE CHROMATOGRAPHY

CROSS REFERENCE TO RELATED APPLICATIONS

This application is a continuation application of U.S. patent application Ser. No. 12/260,623, filed Oct. 29, 2008, now abandoned, which claims priority to and the benefit of U.S. Provisional Patent Application No. 60/983,825, filed Oct. 30, 2007, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: SEQ.TXT, date recorded: Oct. 29, 2008, size: 2.3KB).

BACKGROUND OF THE INVENTION

Field of the Invention

This invention relates generally to protein purification. In particular, the invention relates to a method for purifying antibody from a composition comprising the antibody and at least one contaminant using cation exchange chromatography, wherein a high pH wash step is used to remove contaminants prior to eluting the desired antibody using an elution buffer with increased conductivity.

Description of the Related Art

The large-scale, economic purification of proteins is an increasingly important problem for the biotechnology industry. Generally, proteins are produced by cell culture, using either eukaryotic or prokaryotic cell lines engineered to produce the protein of interest by insertion of a recombinant plasmid containing the gene for that protein. Since the cells typically used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be cased to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through".

Ion exchange chromatography is a chromatographic technique that is commonly used for the purification of proteins. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). In the past, these changes have been progressive; i.e., the pH or conductivity is increased or decreased in a single direction U.S. Pat. Nos. 6,339,142, 6,417,355, 6,489,447, and 7,074,404 (Basey et al.) describe ion exchange chromatography for purifying polypeptides. U.S. Pat. Nos. 6,127,526, 6,333,398, and 6,797,814 (Blank, G.) describe purifying proteins, such as anti-HER2 antibodies, by Protein A chromatography. Methods for purifying proteins, such as antibodies, by ion exchange chromatography are described in US Application Publication No. 2004/0082047.

U.S. Pat. No. 5,110,913 refers to purifying an antibody in an aqueous solution by binding the antibody to an ion exchange resin at a first pH of 4.6, washing at a second pH of 5.5, and eluting the antibody at pH 6.5, wherein the ionic strength of the solutions of these three steps remains constant. Zhang et al. refer to Q membrane, anion exchange chromatography of a human antibody (Zhang et al. "Q Membrane Chromatography Application for Human Antibody Purification Process," Poster presented at *BioProduction*, October 26-27, 2004 Munich, Germany). Other publications concerning protein purification include: Barnthouse et al. *J. Biotech.* 66: 125-136 (1998); Blank et al. *Bioseparation* 10: 65-71 (2001); Follman and Fahrner *J. Chromatog.* 1024: 79-85 (2004); Iyer et al. *BioPharm* 15(1):14-16, 18, 20, 53 (2002); US 2004/0082047A1; EP 333,574; EP 460, 426 B1; EP 556,083; WO 89/05157; WO 92/22653; WO 93/06217; WO 95/22389; WO 96/33208; WO 96/40883; U.S. Pat. No. 4,753,894; U.S. Pat. No. 4,966,851; U.S. Pat. No. 5,110,913; U.S. Pat. No. 5,112,951; U.S. Pat. No. 5,115,101; U.S. Pat. No. 5,118,796; U.S. Pat. No. 5,169,774; U.S. Pat. No. 5,196,323; U.S. Pat. No. 5,256,769; U.S. Pat. No. 5,279,823; U.S. Pat. No. 5,429,746; U.S. Pat. No. 5,451,662; U.S. Pat. No. 5,525,338; U.S. Pat. No. 5,677,171; U.S. Pat. No. 6,005,081; U.S. Pat. No. 6,054,561; U.S. Pat. No. 6,127,526; U.S. Pat. No. 6,267,958; U.S. Pat. No. 6,339,142; U.S. Pat. No. 6,417,335; U.S. Pat. No. 6,489,447; Adachi et al., *Journal of Chromatography. A.* 763(1-2):57-63 (Feb. 28, 1997); Gagnon, P., *Purification Tools for Monoclonal Antibodies*, Tucson:Validated Biosystems, Inc., Chapter 4, pps. 57-86 (1996); Graf et al., *Bioseparation* 4(1):7-20 (February 1994); Mhatre et al., *Journal of Chromatography A* 707(2):225-231 (Jul. 21, 1995); Neidhardt et al., *Journal of Chromatography* 590(2):255-261 (1992); *Protein Purification Applications—A Practical Approach*, Harris and Angal, IRL Press pps. 151-156 (1995); Sofer et al. *Handbook of Process Chromatography: A Guide to Optimization, Scale-up, and Validation*, San Diego:Academic Press pps. 65-80 (1997); Tishchenko et al., *Journal of Chromatography B* 706(1):157-166 (Feb. 27, 1998).

SUMMARY OF THE INVENTION

The invention herein concerns an improved method for cation exchange chromatography of antibodies in which a high pH wash step is used to remove contaminants prior to eluting the desired antibody product. The process results, amongst other things, in improved removal of Chinese Hamster Ovary Proteins (CHOP) contaminants.

According to a first aspect, the invention provides a method for purifying an antibody from a composition comprising the antibody and at least one contaminant, which method comprises the sequential steps of:
  (a) loading the composition onto a cation exchange material wherein the composition is at a first pH;
  (b) washing the cation exchange material with a first wash buffer at a pH which is greater than that of the composition in (a), wherein the pH of the first wash buffer is from about 6.8 to about 9.0;
  (c) washing the cation exchange material with a second wash buffer at a pH which is less than that of the first wash buffer; and
  (d) eluting the antibody from the cation exchange material with an elution buffer at a conductivity which is substantially greater than that of the second wash buffer.

Preferably the antibody binds human CD20, such as rituximab, or binds human vascular endothelial growth factor (VEGF), such as bevacizumab.

According to one preferred embodiment, the invention concerns a method for purifying an antibody that binds human CD20 from a composition comprising the antibody and one or more contaminants selected from the group consisting of Chinese Hamster Ovary Proteins (CHOP), leached protein A, DNA, and aggregated CD20 antibody, which method comprises the sequential steps of:
  (a) loading the composition onto a cation exchange material wherein the composition is at a pH from about 4.0 to about 6.0;
  (b) washing the cation exchange material with a first wash buffer at a pH from about 6.8 to about 9.0;
  (c) washing the cation exchange material with a second wash buffer at a pH from about 5.0 to about 6.0; and
  (d) eluting the antibody from the cation exchange material using an elution buffer with a pH from about 5.0 to about 6.0 and a conductivity from about 10 to about 100 mS/cm. Preferably the CD20 antibody is rituximab.

According to another preferred embodiment, the invention relates to a method for purifying an antibody that binds human vascular endothelial growth factor (VEGF) from a composition comprising the antibody and one or more contaminants selected from the group consisting of a cell culture media component, garamycin, Chinese Hamster Ovary Proteins (CHOP), DNA, viral contaminant, and aggregated VEGF antibody, which method comprises the sequential steps of:
  (a) loading the composition onto a cation exchange material wherein the composition is at a pH from about 4.0 to about 6.0;
  (b) washing the cation exchange material with a first wash buffer at a pH from about 6.8 to about 8.0;
  (c) washing the cation exchange material with a second wash buffer at a pH from about 5.0 to about 6.0; and
  (d) eluting the antibody from the cation exchange material using an elution buffer with a pH from about 5.0 to about 6.0 and a conductivity from about 10 to about 100 mS/cm. Preferably, the VEGF antibody is bevacizumab.

The invention also concerns a composition comprising rituximab in a buffer comprising about 25 mM HEPES, at a pH of about 7.8.

In addition, the invention provides a composition comprising bevacizumab in a buffer comprising about 25 mM MOPS at a pH of about 7.0.

BRIEF DESCRIPTION OF THE DRAWINGS

FIGS. 1A and 1B provide the amino acid sequences of the heavy chain (SEQ ID No. 1) and light chain (SEQ ID No. 2) of rituximab antibody. Each of the framework regions (FR1-4) and each of the CDR regions (CDR1-3) in each variable region are identified, as are the human gamma 1 heavy chain constant sequence and human kappa light chain constant sequence. The variable heavy (VH) region is in SEQ ID No. 3. The variable light (VL) region is in SEQ ID No. 4. The sequence identifiers for the CDRs are: CDR H1 (SEQ ID No. 5), CDR H2 (SEQ ID No. 6), CDR H3 (SEQ ID No. 7), CDR L1 (SEQ ID No. 8), CDR L2 (SEQ ID No. 9), and CDR L3 (SEQ ID No. 10).

FIGS. 2A and 2B provide the amino acid sequences of the heavy chain (SEQ ID No. 11) and light chain (SEQ ID No. 12) of bevacizumab antibody. The end of each variable region is indicated with ‖. The variable heavy (VH) region is in SEQ ID No. 13. The variable light (VL) region is in SEQ ID No. 14. Each of the three CDRs in each variable region is underlined. The sequence identifiers for the CDRs are: CDR H1 (SEQ ID No. 15), CDR H2 (SEQ ID No. 16), CDR H3 (SEQ ID No. 17), CDR L1 (SEQ ID No. 18), CDR L2 (SEQ ID No. 19), and CDR L3 (SEQ ID No. 20).

FIG. 3 provides a side-by-side comparison of host cell proteins removal by the cation exchange chromatography process of the improved rituximab process compared to the original process. Superior CHOP removal was achieved with the new process.

DETAILED DESCRIPTION OF THE PREFERRED EMBODIMENT

Definitions

Herein, numerical ranges or amounts prefaced by the term "about" expressly include the exact range or exact numerical amount.

The "composition" to be purified herein comprises the antibody of interest and one or more contaminants. The composition may be "partially purified" (i.e. having been subjected to one or more purification steps) or may be obtained directly from a host cell or organism producing the antibody (e.g. the composition may comprise harvested cell culture fluid).

As used herein, "polypeptide" refers generally to peptides and proteins having more than about ten amino acids. Preferably, the polypeptide is a mammalian protein, examples of which include: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides as well as antibodies, including antibody fragments, binding to any of the above-listed polypeptides. A preferred polypeptide is an intact antibody or an antibody fragment that binds to human CD20, for example, rituximab; or an intact antibody or an antibody fragment that binds to human vascular endothelial growth factor (VEGF), for example bevacizumab.

A "contaminant" is a material that is different from the desired antibody product. The contaminant includes, without limitation: host cell materials, such as Chinese Hamster Ovary Proteins (CHOP); leached protein A; nucleic acid; a variant, fragment, aggregate or derivative of the desired antibody; another polypeptide; endotoxin; viral contaminant; cell culture media component (e.g. garamycin; GENTAMYCIN®) etc.

The phrase "cation exchange material" refers to a solid phase that is negatively charged and has free cations for exchange with cations in an aqueous solution passed over or through the solid phase. The charge may be provided by attaching one or more charged ligands to the solid phase, e.g. by covalent linking. Alternatively, or in addition, the charge may be an inherent property of the solid phase (e.g. as is the case for silica, which has an overall negative charge). Commercially available cation exchange materials include carboxy-methyl-cellulose, BAKERBOND ABX™, sulphopropyl (SP) immobilized on agarose (e.g. SP-SEPHAROSE FAST FLOW™, SP-SEPHAROSE FAST FLOW XL™ or SP-SEPHAROSE HIGH PERFORMANCE™, from GE Healthcare), CAPTO S™ (GE Healthcare), FRACTOGEL-SO3™, FRACTOGEL-SE HICAP™, and FRACTOPREP™ (EMD Merck), sulphonyl immobilized on agarose (e.g. S-SEPHAROSE FAST FLOW™ from GE Healthcare), and SUPER SP™ (Tosoh Biosciences). A preferred cation exchange material herein comprises cross-linked poly(styrene-divinylbenzene) flow-through particles (solid phase) coated with a polyhydroxylated polymer functionalized with sulfopropyl groups (for example, POROS 50 HS® chromatography resin).

By "solid phase" is meant a non-aqueous matrix to which one or more charged ligands can adhere. The solid phase may be a purification column (including, without limitation, expanded bed and packed bed columns), a discontinuous phase of discrete particles, a membrane, or filter etc. Examples of materials for forming the solid phase include polysaccharides (such as agarose and cellulose) and other mechanically stable matrices such as silica (e.g. controlled pore glass), poly(styrene-divinylbenzene), polyacrylamide, ceramic particles and derivatives of any of the above.

The term "load" herein refers to the composition loaded onto the cation exchange material. Preferably, the cation exchange material is equilibrated with an equilibration buffer prior to loading the composition which is to be purified.

A "buffer" is a solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., Ed. Calbiochem Corporation (1975).

An "equilibration buffer" is a buffer that is used to equilibrate the cation exchange material, prior to loading the composition comprising the antibody of interest and one or more contaminants onto the cation exchange material. Preferably the pH of the equilibration buffer herein is in the range from about 5.0 to about 6.0, preferably about 5.5. Preferably, the conductivity of the equilibration buffer herein is in the range from about 1 to about 8 mS/cm, preferably from about 4 to about 8 mS/cm, and most preferably from about 5 to about 8 mS/cm. Optionally, the equilibration buffer comprises a salt, such as NaCl, for example, in an amount from about 40 mM to about 80 mM, preferably about 60 mM NaCl.

The term "wash buffer" is used herein to refer to the buffer that is passed over the cation exchange material following loading of a composition and prior to elution of the protein of interest. The wash buffer may serve to remove one or more contaminants from the cation exchange material, without substantial elution of the desired antibody product. According to the preferred embodiment of the invention herein a "first wash buffer" and a "second wash buffer" are used.

Herein, the expression "first wash buffer" refers to a wash buffer having a pH increased relative to the pH of the load and/or equilibration buffer. The first wash buffer may be used herein to elute one or more contaminants from the cation exchange material, without substantially eluting the antibody product of interest therefrom. The term "first" should not be interpreted as excluding the use of one or more additional wash or other buffers between the load and the first wash buffer. Preferably the pH of the first wash buffer herein is in the range from about 6.8 to about 9.0, preferably from about 7.0 to about 8.0, and most preferably pH about 7.0 or pH about 7.8. Preferably, the conductivity of the first wash buffer herein is in the range from about 0.01 to about 5 mS/cm, preferably from about 0.1 to about 3 mS/cm, and most preferably from about 0.2 to about 2 mS/cm. Optionally, the first wash buffer is substantially free of a salt (such as NaCl) therein.

The expression "second wash buffer" for the purposes of this application refers to a wash buffer used after the first wash buffer to prepare the cation exchange material for elution of the antibody of interest. The term "second" should not be interpreted as excluding the use of one or more additional wash or other buffers between the first wash buffer and second wash buffer. Preferably the pH of the second wash buffer herein is in the range from about 5.0 to about 6.0, preferably about 5.5, and most preferably pH 5.5. Preferably, the conductivity of the second wash buffer herein is in the range from about 0.01 to about 5 mS/cm, preferably about 0.1 to about 3 mS/cm, and most preferably from about 0.5 to about 3.0 mS/cm.

"Elution buffer" is used to elute the antibody of interest from the solid phase. Herein, the elution buffer has a substantially increased conductivity relative to that of the second wash buffer, such that the desired antibody product is eluted from the cation exchange material. Preferably, the conductivity of the elution buffer is substantially greater than that of the load and of each of the preceding buffers, namely of the equilibration buffer, first wash buffer, and second wash buffer. By "substantially greater" conductivity is meant, for example, that the buffer has a conductivity which is at least 2, 3, 4, 5 or 6 conductivity units (mS/cm) greater than that of the composition or buffer to which it is being compared. In one embodiment, the pH of the elution buffer is substantially the same as that of the equilibration and/or second wash buffer. Preferably the pH of the elution buffer herein is in the range from about 5.0 to about 6.0, preferably about 5.5, and most preferably pH 5.5. Preferably, the conductivity of the elution buffer herein is in the range from about 10 mS/cm to about 100 mS/cm, preferably from about 12 mS/cm to about 30 mS/cm, and most preferably from about 12 to about 20 mS/cm. Increased conductivity may be achieved by the addition of a salt, such as sodium chloride, sodium acetate, potassium chloride to the elution buffer. Preferably, the elution buffer comprises from about 100 to about 300 mM NaCl, preferably from about 150 mM to about 200 mM NaCl, for example about 175 mM NaCl or about 160 mM NaCl.

A "regeneration buffer" may be used to regenerate the cation exchange material such that it can be re-used. The regeneration buffer has a conductivity and/or pH as required to remove substantially all contaminants and the antibody of interest from the cation exchange material.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

By "purifying" an antibody from a composition comprising the antibody and one or more contaminants is meant increasing the degree of purity of the antibody in the composition by removing (completely or partially) at least one contaminant from the composition. A "purification step" may be part of an overall purification process resulting in a "homogeneous" composition. "Homogeneous" is used herein to refer to a composition comprising at least about 70% by weight of the antibody of interest, based on total weight of the composition, preferably at least about 80% by weight, more preferably at least about 90% by weight, even more preferably at least about 95% by weight.

By "binding" a molecule to a cation exchange material is meant exposing the molecule to the cation exchange material under appropriate conditions (pH and/or conductivity) such that the molecule is reversibly immobilized in or on the cation exchange material by virtue of ionic interactions between the molecule and a charged group or charged groups of the cation exchange material.

By "washing" the cation exchange material is meant passing an appropriate buffer through or over the cation exchange material.

By "eluting" a molecule (e.g. antibody or contaminant) from a cation exchange material is meant to remove the molecule therefrom.

In preferred embodiments of the invention, the antibody to be purified herein is a recombinant antibody. A "recombinant antibody" is one which has been produced in a host cell which has been transformed or transfected with nucleic acid encoding the antibody, or produces the antibody as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a host animal. Methods for recombinant production of polypeptides are described in U.S. Pat. No. 5,534,615, expressly incorporated herein by reference, for example.

A "variant" or "amino acid sequence variant" of a starting polypeptide is a polypeptide that comprises an amino acid sequence different from that of the starting polypeptide. Generally, a variant will possess at least 80% sequence identity, preferably at least 90% sequence identity, more preferably at least 95% sequence identity, and most preferably at least 98% sequence identity with the native polypeptide. Percentage sequence identity is determined, for example, by the Fitch et al., *Proc. Natl. Acad. Sci. USA* 80:1382-1386 (1983), version of the algorithm described by Needleman et al., *J. Mol. Biol.* 48:443-453 (1970), after aligning the sequences to provide for maximum homology. Amino acid sequence variants of a polypeptide may be prepared by introducing appropriate nucleotide changes into DNA encoding the polypeptide, or by peptide synthesis. Such variants include, for example, deletions from, and/or insertions into and/or substitutions of, residues within the amino acid sequence of the polypeptide of interest. Any combination of deletion, insertion, and substitution is made to arrive at the final construct, provided that the final construct possesses the desired characteristics. The amino acid changes also may alter post-translational processing of the polypeptide, such as by changing the number or position of glycosylation sites. Other post-translational modifications include hydroxylation of proline and lysine, phosphorylation of hydroxyl groups of seryl, threonyl or tyrosyl residues, methylation of the α-amino groups of lysine, arginine and histidine side chains (T. E. Creighton, Proteins: Structure and Molecular Properties, W.H. Freeman & Co., San Francisco, pp. 79-86 (1983)). Methods for generating amino acid sequence variants of polypeptides are described in U.S. Pat. No. 5,534,615, expressly incorporated herein by reference, for example.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired binding specificity.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the HER receptor family such as the EGF receptor (HER1), HER2, HER3 or HER4 receptor; cell adhesion molecules such as LFA-1, Mac1, p150,95, VLA-4, ICAM-1, VCAM and av/b3 integrin including either a or b subunits thereof (e.g. anti-CD 11a, anti-CD 18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Examples of antibodies to be purified herein include, but are not limited to: HER2 antibodies including trastuzumab (HERCEPTIN®) (Carter et al., *Proc. Natl. Acad. Sci. USA*, 89:4285-4289 (1992), U.S. Pat. No. 5,725,856) and pertuzumab (OMNITARG™) (WO01/00245); CD20 antibodies (see below); IL-8 antibodies (St John et al., *Chest*, 103:932 (1993), and International Publication No. WO 95/23865); VEGF or VEGF receptor antibodies including humanized and/or affinity matured VEGF antibodies such as the humanized VEGF antibody huA4.6.1 bevacizumab (AVASTIN®) and ranibizumab (LUCENTIS®) (Kim et al., *Growth Factors*, 7:53-64 (1992), International Publication No. WO 96/30046, and WO 98/45331, published Oct. 15, 1998); PSCA antibodies (WO01/40309); CD11a antibodies including efalizumab (RAPTIVA®) (U.S. Pat. No. 5,622,700, WO 98/23761, Steppe et al., *Transplant Intl.* 4:3-7 (1991), and Hourmant et al., *Transplantation* 58:377-380 (1994)); antibodies that bind IgE including omalizumab (XOLAIR®) (Presta et al., *J. Immunol.* 151:2623-2632 (1993), and International Publication No. WO 95/19181; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); CD18 antibodies (U.S. Pat. No. 5,622,700, issued Apr. 22, 1997, or as in WO 97/26912, published Jul. 31, 1997); Apo-2 receptor antibody antibodies (WO 98/51793 published Nov. 19, 1998); Tissue Factor (TF) antibodies (European Patent No. 0 420 937 B1 granted Nov. 9, 1994); α4-α7 integrin antibodies (WO 98/06248 published Feb. 19, 1998); EGFR antibodies (e.g. chimerized or humanized 225 antibody, cetuximab, ERBUTIX® as in WO 96/40210 published Dec. 19, 1996); CD3 antibodies such as OKT3 (U.S. Pat. No. 4,515,893 issued May 7, 1985); CD25 or Tac antibodies such as CHI-621 (SIMULECT®) and ZENAPAX® (See U.S. Pat. No. 5,693,762 issued Dec. 2, 1997); CD4 antibodies such as the cM-7412 antibody (Choy et al. *Arthritis Rheum* 39(1): 52-56 (1996)); CD52 antibodies such as CAMPATH-1H (ILEX/Berlex) (Riechmann et al. *Nature* 332:323-337 (1988)); Fc receptor antibodies such as the M22 antibody directed against FcγRI as in Graziano et al. *J. Immunol.* 155(10):4996-5002 (1995); carcinoembryonic antigen (CEA) antibodies such as hMN-14 (Sharkey et al. *Cancer Res.* 55(23Suppl): 5935s-5945s (1995)); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); CD38 antibodies, e.g. AT 13/5 (Ellis et al. *J. Immunol.* 155(2):925-937 (1995)); CD33 antibodies such as Hu M195 (Jurcic et al. *Cancer Res* 55(23 Suppl):5908s-5910s (1995)) and CMA-676 or CDP771; EpCAM antibodies such as 17-1A (PANOREX®); GpIIb/IIIa antibodies such as abciximab or c7E3 Fab (REOPRO®); RSV antibodies such as MEDI-493 (SYNAGIS®); CMV antibodies such as PROTOVIR®; HIV antibodies such as PRO542; hepatitis antibodies such as the Hep B antibody OSTAVIR®; CA 125 antibody OvaRex; idiotypic GD3 epitope antibody BEC2; αvβ3 antibody (e.g. VITAXIN®; Medimmune); human renal cell carcinoman antibody such as ch-G250; 1NG-1; anti-human 17-1An antibody (3622W94); anti-human colorectal tumor antibody (A33); anti-human melanoman antibody R24 directed against GD3 ganglioside; anti-human squamous-cell carcinoma (SF-25); human leukocyte antigen (HLA) antibody such as Smart ID10 and the anti-HLA DR antibody Oncolym (Lym-1); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody, such as Lym-1Y-90 (USC) or anti-Lym-1 Oncolym (USC/Peregrine); LIF 226 (Enhanced Lifesci.); BAFF antibody (e.g., WO 03/33658); BAFF receptor antibody (see e.g., WO 02/24909); BR3 antibody; Blys antibody such as belimumab; LYMPHOSTAT-B™; ISF 154 (UCSD/Roche/Tragen); gomiliximab (Idec 152; Biogen Idec); IL-6 receptor antibody such as atlizumab (ACTEMRA™; Chugai/Roche); IL-15 antibody such as HuMax-11-15 (Genmab/Amgen); chemokine receptor antibody, such as a CCR2 antibody (e.g. MLN1202; Millieneum); anti-complement antibody, such as C5 antibody (e.g. eculizumab, 5G1.1; Alexion); oral formulation of human immunoglobulin (e.g. IgPO; Protein Therapeutics); IL-12 antibody such as ABT-874 (CAT/Abbott); Teneliximab (BMS-224818; BMS); CD40 antibodies, including S2C6 and humanized variants thereof (WO00/75348) and TNX 100 (Chiron/Tanox); TNF-α antibodies including cA2 or infliximab (REMICADE®), CDP571, MAK-195, adalimumab (HUMIRA™), pegylated TNF-α antibody fragment such as CDP-870 (Celltech), D2E7 (Knoll), anti-TNF-α polyclonal antibody (e.g. PassTNF; Verigen); CD22 antibodies such as LL2 or epratuzumab (LYMPHOCIDE®; Immunomedics), including epratuzumab Y-90 and epratzumab I-131, Abiogen's CD22 antibody (Abiogen, Italy), CMC 544 (Wyeth/Celltech), combotox (UT Soutwestern), BL22 (NIH), and LympoScan Tc99 (Immunomedics). Preferably, the antibody that is purified herein is a naked, intact antibody which binds to human CD20, or a naked, intact antibody which binds to human VEGF.

The human "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., *Proc. Natl. Acad. Sci.* (USA) 82:1766 (1985), for example.

A "CD20 antibody antagonist" herein is an antibody that, upon binding to CD20 on B cells, destroys or depletes B cells in a subject and/or interferes with one or more B-cell functions, e.g., by reducing or preventing a humoral response elicited by the B cell. The antibody antagonist preferably is able to deplete B cells (i.e., reduce circulating B-cell levels) in a subject treated therewith. Such depletion may be achieved via various mechanisms such antibody-dependent cell-mediated cytotoxicity (ADCC) and/or complement-dependent cytotoxicity (CDC), inhibition of B-cell proliferation and/or induction of B-cell death (e.g., via apoptosis).

As used herein, "B cell depletion" refers to a reduction in B cell levels in an animal or human generally after drug or antibody treatment, as compared to the level before treatment. B cell depletion can be partial or complete. B cell levels are measurable using well known techniques such as those described in Reff et al., *Blood* 83: 435-445 (1994), or U.S. Pat. No. 5,736,137 (Anderson et al.). By way of example, a mammal (e.g. a normal primate) may be treated with various dosages of the antibody or immunoadhesin, and peripheral B-cell concentrations may be determined, e.g. by a FACS method that counts B cells.

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine 1131 tositumomab" antibody (BEXXAR™) commercially available from Corixa (see, also, U.S. Pat. No. 5,595,721); murine monoclonal antibody "1F5" (Press et al. *Blood* 69(2):584-591 (1987) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); humanized 2H7 (WO 2004/056312, Lowman et al., and as set forth below); 2F2 (HuMax-CD20), a fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003); WO 2004/035607; US2004/0167319); the human monoclonal antibodies set forth in WO 2004/035607 and US2004/0167319 (Teeling et al.); the antibodies having complex N-glycoside-linked sugar chains bound to the Fc region described in US 2004/0093621 (Shitara et al.); monoclonal antibodies and antigen-binding fragments binding to CD20 (WO 2005/000901, Tedder et al.) such as HB20-3, HB20-4, HB20-25, and MB20-11; CD20 binding molecules such as the AME series of antibodies, e.g., AME 33 antibodies as set forth in WO 2004/103404 and US2005/0025764 (Watkins et al., Eli Lilly/Applied Molecular Evolution, AME); CD20 binding molecules such as those described in US 2005/0025764 (Watkins et al.); A20 antibody or variants thereof such as chimeric or humanized A20 antibody (cA20, hA20, respectively) or IMMU-106 (US 2003/0219433, Immunomedics); CD20-binding antibodies, including epitope-depleted Leu-16, 1H4, or 2B8, optionally conjugated with IL-2, as in US 2005/0069545A1 and WO 2005/16969 (Carr et al.); bispecific antibody that binds CD22 and CD20, for example, hLL2xhA20 (WO2005/14618, Chang et al.); monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)); 1H4 (Haisma et al. *Blood* 92:184 (1998)); anti-CD20 auristatin E conjugate (Seattle Genetics); anti-CD20-IL2 (EMD/Biovation/City of Hope); anti-CD20 MAb therapy (EpiCyte); anti-CD20 antibody TRU 015 (Trubion). The preferred CD20 antibodies herein are chimeric, humanized, or human CD20 antibodies, more preferably rituximab, humanized 2H7, 2F2 (Hu-Max-CD20) human CD20 antibody (Genmab), and humanized A20 or IMMUN-106 antibody (Immunomedics).

For the purposes herein, the terms "rituximab," "RITUXAN®," and "C2B8" herein refer to a recombinant chimeric antibody which binds to the human CD20 antigen as described in U.S. Pat. No. 5,736,137, Anderson et al. Such antibody preferably comprises a heavy chain comprising CDR H1 (SEQ ID No. 5), CDR H2 (SEQ ID No. 6), CDR H3 (SEQ ID No. 7), and a light chain, wherein the light chain preferably comprises CDR L1 (SEQ ID No. 8), CDR L2 (SEQ ID No. 9), and CDR L3 (SEQ ID No. 10); preferably the heavy chain comprises a variable heavy (VH) region comprising SEQ ID No. 3 and a variable light (VL) region comprising SEQ ID No. 4; and most preferably comprises a heavy chain comprising SEQ ID No. 1 (with or without a C-terminal lysine residue), and a light chain, wherein the light chain preferably comprises SEQ ID No. 2. The terms expressly include variant forms such as described in Moorhouse et al. *J. Pharm Biomed. Anal.* 16:593-603 (1997).

The term "human VEGF" as used herein refers to the 165-amino acid human vascular endothelial cell growth factor, and related 121-, 189-, and 206-amino acid vascular endothelial cell growth factors, as described by Leung et al., *Science* 246:1306 (1989), and Houck et al., *Mol. Endocrin.* 5:1806 (1991) together with the naturally occurring allelic and processed forms of those growth factors.

The present invention provides anti-VEGF antagonistic antibodies which are capable of inhibiting one or more of the biological activities of VEGF, for example, its mitogenic or angiogenic activity. Antagonists of VEGF act by interfering with the binding of VEGF to a cellular receptor, by incapacitating or killing cells which have been activated by VEGF, or by interfering with vascular endothelial cell activation after VEGF binding to a cellular receptor. All such points of intervention by a VEGF antagonist shall be considered equivalent for purposes of this invention.

For the purposes herein, the terms "bevacizumab," "AVASTIN®," "F(ab)-12," and "rhuMAb VEGF" herein refer to a recombinant humanized monoclonal antibody which binds human vascular endothelial growth factor (VEGF) antigen (rhuMAb VEGF) as described in U.S. Pat. No. 7,169,901, Presta et al. Such antibody preferably comprises a heavy chain comprising CDR H1 (SEQ ID No. 15), CDR H2 (SEQ ID No. 16), CDR H3 (SEQ ID No. 17), and a light chain, wherein the light chain preferably comprises CDR L1 (SEQ ID No. 18), CDR L2 (SEQ ID No. 19), and CDR L3 (SEQ ID No. 20); most preferably the heavy chain comprises a variable heavy (VH) region comprising SEQ ID No. 13 and a variable light (VL) region comprising SEQ ID No. 14; and preferably comprises a heavy chain comprising SEQ ID No. 11 (with or without a C-terminal lysine residue), and a light chain, wherein the light chain preferably comprises SEQ ID No. 12. The terms expressly include variant forms that form during production of the recombinant antibody product.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Polypeptides of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immuno globulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)).

Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). In another embodiment, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. *Polypeptide Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Antibodies with more than two valencies are contemplated. For example, trispecific antibodies can be prepared. Tutt et al. *J. Immunol.* 147: 60 (1991).

A "naked antibody" for the purposes herein is an antibody that is not conjugated to a cytotoxic moiety or radiolabel.

An "intact antibody" herein is one which comprises two antigen binding regions, and an Fc region. Preferably, the intact antibody has a functional Fc region.

"Treatment" refers to both therapeutic treatment and prophylactic or preventative measures. Those in need of treatment include those already with the disorder as well as those in which the disorder is to be prevented.

A "disorder" is any condition that would benefit from treatment with the antibody purified as described herein. This includes both chronic and acute disorders and diseases and those pathological conditions which predispose the mammal to the disorder in question.

The word "label" when used herein refers to a detectable compound or composition which is conjugated directly or indirectly to the antibody. The label may be itself be detectable (e.g., radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small-molecule toxins or enzymatically active toxins of bacterial, fungal, plant or animal origin, or fragments thereof.

MODES FOR CARRYING OUT THE INVENTION

The invention herein provides methods for purifying an antibody from a composition (e.g. an aqueous solution) comprising the antibody and one or more contaminants. The composition is generally one resulting from the recombinant production of the antibody, but may be that resulting from production of the antibody by peptide synthesis (or other synthetic means) or the antibody may be purified from a native source of the antibody. Preferably the antibody binds human CD20 antigen, such as rituximab, or binds human VEGF antigen, such as bevacizumab.

Recombinant Production of Antibodies

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g. as described in U.S. Pat. No. 5,534,615, specifically incorporated herein by reference).

Suitable host cells for cloning or expressing the DNA in the vectors herein are the prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include, but are not limited to, monkey kidney CV1 cells transformed by SV40 (COS-7, ATCC CRL 1651); human embryonic kidney cells (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and human hepatoma cells (Hep G2). Often, CHO cells are preferred for the expression of antibodies, and may be advantageously used to produce the antibodies purified in accordance with the present invention.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as garamycin; GENTAMYCIN®), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells (e.g. resulting from homogenization), is removed, for example, by centrifugation or ultrafiltration. Where the antibody is secreted into the medium, supernatants from such expression systems may be concentrated using a commercially available protein concentration filter, for example, an Amicon or Millipore Pellicon ultrafiltration unit.

The Cation Exchange Chromatography Method of the Invention

In the preferred embodiment of the invention, the composition to be subjected to the purification method herein is a recombinantly produced antibody, preferably an intact antibody, expressed by a Chinese Hamster Ovary (CHO) recombinant host cell culture. Optionally, the composition has been subjected to at least one purification step prior to cation exchange chromatography. The composition contains the antibody of interest and one or more contaminants, such as Chinese Hamster Ovary Proteins (CHOP); leached protein A; nucleic acid; a variant, fragment, aggregate or derivative of the desired antibody; another polypeptide; endotoxin; viral contaminant; cell culture media component (e.g. garamycin; GENTAMYCIN®), etc.

Examples of additional purification procedures which may be performed prior to, during, or following the cation exchange chromatography method include fractionation on a hydrophobic interaction chromatography (e.g. on PHENYL-SEPHAROSE™), ethanol precipitation, isoelectric focusing, Reverse Phase HPLC, chromatography on silica, chromatography on HEPARIN SEPHAROSE™, anion exchange chromatography, further cation exchange chromatography, mixed-mode ion exchange, chromatofocusing, SDS-PAGE, ammonium sulfate precipitation, hydroxyapatite chromatography, gel electrophoresis, dialysis, hydrophic charge induction chromatography, and affinity chromatography (e.g. using protein A, protein G, an antibody, or a specific substrate, ligand or antigen as the capture reagent).

According to the present invention, the cation exchange purification scheme typically includes the following steps performed sequentially: (1) equilibration of the cation exchange material; (2) loading the composition to be purified onto the cation exchange material, (3) a first wash step; (4) a second wash step, and (5) elution of the antibody of interest.

By including at least two wash steps in the cation exchange purification scheme, at least the first of which is conducted at high pH (about pH 6.8 or greater), the efficacy of purification can be significantly improved. In particular, performing the first wash step using a wash buffer with a pH in the range from about 6.8 to about 9.0 (e.g. from about 7.0 to 8.0), such as, for example, about pH 7.8 or about pH 7.0, contaminants as described above are removed more efficiently than using the conventional lower pH range of about 5.0 to about 5.5. As a result, the host cell protein content of the composition comprising the antibody eluted from the cation exchange material is typically less than about 200 ppm, which is below the approximately 500 ppm level achieved using one wash step at a pH of about 5 to 5.5.

In the preferred embodiment of the invention, the cation exchange material comprises cross-linked poly(styrene-divinylbenzene) flow-through particles (solid phase) coated with a polyhydroxylated polymer functionalized with sulfopropyl groups, for example, a POROS 50 HS® column available from Applied Biosystems. Usually, an equilibration buffer is passed over or through the cation exchange material prior to loading the composition comprising the antibody of interest and one or more contaminants onto the material. In the preferred embodiment of the invention, the equilibration buffer has a pH from about 5.0 to about 6.0, for example about pH 5.5. One exemplary equilibration buffer comprises 19 mM MES, 60 mM NaCl, pH 5.50. Another exemplary equilibration buffer comprises 23 mM MES, 60 mM NaCl, pH 5.50.

Following equilibration, an aqueous solution comprising the antibody of interest and one or more contaminants is loaded onto the cation exchange material. Optionally, the pH of the load is in the range from about 4.0 to about 6.0, for example about pH 5.0 or about pH 5.5. In a preferred embodiment, a conditioned product pool from a prior purification step is loaded. In one embodiment, a Protein A pool from a prior Protein A chromatography purification, pH 5.0 is loaded on the cation exchange material. In another embodiment, a conditioned Q-SEPHAROSE® pool, pH 5.5 is loaded onto the cation exchange material. Exemplary load densities are in the range from about 10 to about 100 g/L resin, preferably from about 10 to about 60 g/L resin, most preferably from about 15 to about 45 g/L resin. The antibody of interest is bound to the cation exchange material as a result of this loading step.

After loading, the cation exchange material is washed in a first wash step with a first wash buffer. During the wash process, wash buffer is passed over the cation exchange material. The composition of the wash buffer is typically chosen to elute as many contaminants as possible from the resin without eluting a substantial amount of the antibody of interest. The pH of the first wash buffer is generally higher than that of the equilibration buffer and/or of the loaded composition, for example about 2 to about 3 pH units higher. Preferably the pH of the first wash buffer is in the range from about pH 6.8 to about 9.0, preferably from about pH 6.8 to about 8.0, for example about pH 7.8 or about pH 7.0. Examples of buffers which buffer in this pH range include, but are not limited to HEPES, MES, sodium acetate, TRIS/HCl, Triethanolamine hydrochloride/NaOH, Bicine/HCl, Tricine/HCl etc. The preferred first wash buffer comprises or consists of: (1) 25 mM HEPES, pH 7.8 or (2) 25 mM MOPS, pH 7.0.

In this regard, the present invention provides a composition comprising a recombinant chimeric CD20 antibody, such as rituximab, in 25 mM HEPES, pH 7.8. The invention also provides a recombinant humanized VEGF antibody, such as bevacizumab, in 25 mM MOPS, pH 7.0. Such compositions are useful, among other things, as intermediate compositions used in the purification of these products.

The invention herein generally entails at least one further, or a second, wash step using a second wash buffer. The pH of the second wash buffer preferably is lower than that of the first wash buffer, for example from about 2 to about 3 pH units lower. So, for example, the pH of the second wash buffer may be in the range from about pH 5.0 to about pH 6.0. Preferably, the pH of the second wash buffer is about 5.5. Examples of buffers which buffer in this pH range include, but are not limited to, MES, acetic acid/sodium acetate or NaOH, $NaH_2PO_3/Na_2HPO_4$, Bis.Tris/HCl. MES, pH 5.5 is the preferred buffer for the second wash. In one embodiment, the second wash buffer comprises or consists of: 19 mM MES, 10 mM NaCl, pH 5.50. In another embodiment, the second wash buffer comprises or consists of 23 mM MES, 10 mM NaCl, pH 5.50.

While additional wash steps may be employed, preferably only a first and second wash step are performed, prior to eluting the desired antibody. Contaminants such as those discussed above are removed from the cation exchange material during the first and/or second wash step. Preferably, the first wash step removes most of the contaminants.

Following the wash step(s) noted above, the desired antibody is eluted from the cation exchange material. Elution of the antibody may be achieved by increasing the conductivity or ionic strength. Desirably, the conductivity of the elution buffer is greater than about 10 mS/cm. Increased conductivity may be achieved by including a relatively high salt concentration in the elution buffer. Exemplary salts for this purpose include, without limitation, sodium acetate, sodium chloride (NaCl), and potassium chloride (KCl). In one embodiment, the elution buffer comprises from about 100 to about 300 mM NaCl. The elution buffer generally will have approximately the same pH as the second wash buffer. A preferred elution buffer comprises: 19 mM MES, 160 mM NaCl, pH 5.5. Another preferred elution buffer comprises: 23 mM MES, 175 mM NaCl, pH 5.5. Elution preferably involves step elution (as opposed to gradient elution).

While the elution step is optionally followed by a regeneration step, such is not necessary according to the preferred embodiment of the invention.

While additional steps are contemplated, preferably the cation exchange purification method herein consists of only the following steps: equilibration (e.g. using equilibration buffer pH about 5.5), loading a composition comprising antibody and contaminant(s) (e.g. where pH of the loaded composition is about 5.0 or about 5.5), first wash step for eluting contaminants (e.g. using first wash buffer pH about 7.8 or first wash buffer pH about 7.0), second wash step (e.g. using second wash buffer pH about 5.5), and elution (e.g. using elution buffer pH about 5.5, and increased conductivity relative to each of the earlier steps for eluting antibody).

The antibody preparation obtained according to the cation exchange chromatography method herein may be subjected to additional purification steps, if necessary. Exemplary further purification steps have been discussed above.

Optionally, the antibody is conjugated to one or more heterologous molecules as desired. The heterologous molecule may, for example, be one which increases the serum half-life of the antibody (e.g. polyethylene glycol, PEG), or it may be a label (e.g. an enzyme, fluorescent label and/or radionuclide), or a cytotoxic molecule (e.g. a toxin, chemotherapeutic drug, or radioactive isotope etc).

A therapeutic formulation comprising the antibody, optionally conjugated with a heterologous molecule, may be prepared by mixing the antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™

(injectable microspheres composed of lactic acid-glycolic acid copolymer and leuprolide acetate), and poly-D-(−)-3-hydroxybutyric acid.

The antibody purified as disclosed herein or the composition comprising the antibody and a pharmaceutically acceptable carrier is then used for various diagnostic, therapeutic or other uses known for such antibodies and compositions. For example, the antibody may be used to treat a disorder in a mammal by administering a therapeutically effective amount of the antibody to the mammal. In the case of a CD20 antibody such as rituximab it can be used to deplete B-cells, treat lymphoma (for example Non-Hodgkin's Lymphoma, NHL), or leukemia (for example Chronic Lymphocytic Leukemia, CLL) as well as autoimmune diseases such as rheumatoid arthritis (RA), multiple sclerosis (MS), lupus etc. For an antibody that binds to VEGF, such as bevacizumab, it can be used to inhibit angiogenesis, treat cancer, and treat macular degeneration, etc.

The following examples are offered by way of illustration and not by way of limitation. The disclosures of all citations in the specification are expressly incorporated herein by reference.

Example 1: Purification of a CD20 Antibody

This example describes an improved cation exchange chromatography process for purifying a CD20 antibody, rituximab. Rituximab is used for therapy of NHL, CLL, RA, MS, etc. The structure of the Rituximab molecule is disclosed in U.S. Pat. No. 5,736,137, Anderson et al., (expressly incorporated herein by reference) as well as FIGS. 1A-1B herein. Rituximab is commercially available from Genentech, Inc.

Cation-exchange chromatography is used to further reduce the levels of CHOP, DNA, leached protein A, garamycin (GENTAMYCIN®), Rituximab aggregates, and potential viruses. Rituximab binds to the column under the load conditions. The column is then washed, eluted, regenerated/sanitized, and stored until the next use. Multiple cycles may be used to process an entire batch of affinity pool. The cation-exchange pool may be held at room temperature up to 30° C. for up to 3 days or at 5° C. for up to 7 days.

The cation-exchange resin (POROS 50 HS®, Applied Biosystems) is packed in a column to a bed height of 17-33 cm. Before the affinity pool is loaded, the cation-exchange column is purged of storage solution with equilibration buffer. After equilibration, the affinity pool is loaded onto the column. The product binds to the column under these conditions. The column is then washed with wash 1 buffer, followed by wash 2 buffer. Rituximab is eluted from the column using a high-ionic-strength elution buffer.

A comparison of the conditions for the process of the present invention compared to the original (control) process is provided in the following table.

TABLE 1

Comparison of Buffers for Rituximab Cation Exchange Chromatography Processes

| Phase | Buffer composition (original process) | Buffer composition (exemplified process) |
|---|---|---|
| Pre-equilibration | 20 mM MES, 500 mM NaCl, pH 5.50 | None |
| Equilibration | 20 mM MES, 60 mM NaCl, pH 5.50 | 19 mM MES, 60 mM NaCl, pH 5.50 |
| Load | Conditioned Protein A pool, pH 5.00, Load density ≤50 g/L resin | Conditioned Protein A pool, pH 5.00, Load density ≤50 g/L resin |
| Wash 1 | 20 mM MES, 60 mM NaCl, pH 5.50 | 25 mM HEPES, pH 7.80 |
| Wash 2 | None | 19 mM MES, 10 mM NaCl, pH 5.50 |
| Elution | 20 mM MES, 160 mM NaCl, pH 5.50 | 19 mM MES, 160 mM NaCl, pH 5.50 |
| Regeneration | 20 mM MES, 500 mM NaCl, pH 5.50 | None |
| Sanitization | 0.5N NaOH | 0.5N NaOH |
| Storage | 0.1N NaOH | 0.1N NaOH |

The desired pH, conductivity and molarity ranges for the load and buffers in the rituximab process are provided in the following table.

TABLE 2

Preferred pH, Conductivity and Molarity Ranges for Rituximab Process

| Buffer | Buffer Composition | Target pH | Preferred Buffer Molarity Range | Preferred Buffer pH Range | Allowable Conductivity Range for Buffers |
|---|---|---|---|---|---|
| Equilibration | 19 mM MES, 60 mM NaCl | 5.5 | 14-23 mM MES 50-70 mM NaCl | 5.0-6.0 | 5.0-7.2 mS/cm |
| Load | Conditioned Protein A Pool | 5.0 | NA | 4.5-5.5 | 2.5-5.5 mS/cm |
| Wash 1 | 25 mM HEPES | 7.8 | 15-35 mM HEPES | 7.5-8.1 | 0.5-1.5 mS/cm |
| Wash 2 | 19 mM MES 10 mM NaCl | 5.5 | 14-23 mM MES 5-15 mM NaCl | 5.0-6.0 | 0.6-2.2 mS/cm |
| Elution | 19 mM MES 160 mM NaCl | 5.5 | 14-23 mM MES 140-180 mM NaCl | 5.3-5.7 | 13.4-17.2 mS/cm |
| Sanitization | 0.5N NaOH | NA | NA | NA | NA |
| Storage | 0.1N NaOH | NA | NA | NA | NA |

* Conductivity values measured with temperature compensation based on a temperature of 20° C. and an alpha value of 1.77.

The exemplified process for Rituximab purification enhanced the robustness of host cell protein removal by enabling higher removal of host cell proteins in the wash phases, resulting in lower levels of host cell proteins in the product pool (elution pool) and facilitating the removal of the impurities in the subsequent downstream step. FIG. 3 illustrates the advantages of the present process in terms of host cell proteins removal.

Example 2: Purification of a VEGF Antibody

This example describes a cation exchange chromatography process for purifying a recombinant humanized vascular endothelial growth factor antibody (rhuMAb VEGF), bevacizumab. The structure of the bevacizumab molecule is disclosed in U.S. Pat. No. 7,169,901, Presta et al., expressly incorporated herein by reference. See also FIGS. 2A-2B herein. Bevacizumab is commercially available from Genentech, Inc.

This example summarizes the development studies performed on the cation exchange step for an improved bevacizumab purification process. Three cation exchange resins were evaluated in these studies: CM SEPHAROSE FAST FLOW®, SP SEPHAROSE FAST FLOW® and POROS 50HS®. The cation exchange purification processes using these three resins were evaluated with respect to: process performance (impurities removal, retrovirus removal, and step yield), product quality, process robustness and process fit at all current manufacturing sites. Based on the data generated in these studies, POROS 50HS® showed superior process performance and robustness and was selected as the cation exchange resin for the improved purification process.

Cation exchange chromatography is the final chromatography step in the purification process. It serves to remove cell culture media components (garamycin), host cell derived impurities (CHOP, and DNA) and aggregated forms of bevacizumab. It also functions as a viral removal step.

The column is operated in a bind-and-elute mode and is performed at ambient temperature. The column uses a cation exchange resin (POROS 50HS®). The resin consists of a porous, polystyrene-divinylbenzene bed support coupled with a negatively charged functional group. The column is removed from storage by washing with equilibration buffer. The viral filtered pool will be diluted with 0.3 volumes of water for injection (WFI) to meet the conductivity limit of ≤5.5 mS/cm. The viral filtered pool is then loaded onto the equilibrated column. The product binds to the resin. After loading, the column is washed with a high pH buffer to flush the load material through the column and remove CHOP impurities. The column is then washed with a low salt buffer to lower the pH and prepare the column for elution. Product is eluted using a step elution of high salt buffer with a maximum of 7 column volumes. After elution, the column and skid are sanitized with sanitization solution (0.5 N NaOH) prior to storage in storage solution (0.1 N NaOH) until its next use.

The following table provides a description of the conditions for the bevacizumab process of the invention herein.

TABLE 3

Bevacizumab Process

| Phase | Buffer/Solution | Process Parameter | Flow rate (cm/hr) |
| --- | --- | --- | --- |
| Bed Height (cm) | N/A | 30 | N/A |
| Equilibration | 23 mM MES/60 mM NaCl pH 5.5, cond. 6.9 mS/cm | 4 CV | 100 |
| Load | Conditioned Viral Filtered (VF) Pool pH 5.5 ± 0.2, cond. ≤5.5 mS/cm | 15-45 g bevacizumab/ L of resin | 100 |
| Wash 1 | 25 mM MOPS, pH 7.0 | 3 CV | 100 |
| Wash 2 | 23 mM MES/10 mM NaCl pH 5.5, cond. 1.5 mS/cm | 3 CV | 100 |
| Elution | 23 mM MES/175 mM NaCl pH 5.5, cond. 18 mS/cm | 7 CV | 100 |
| | Start Pooling | $OD_{280} \geq 0.5$ | N/A |
| | End Pooling | $OD_{280} \leq 1.0$ | N/A |
| Sanitization | 0.5N NaOH | 3-6 CV | 50-100 |
| Storage | 0.1N NaOH | 3-6 CV | 50-100 |

The desired pH, conductivity and molarity ranges for the load and buffers in the bevacizumab process are provided in the following table.

TABLE 4

Preferred pH, Conductivity and Molarity Ranges for Bevacizumab Process

| | Target buffer | Target pH range | Target conductivity range | Preferred buffer molarity range | Preferred buffer pH range |
| --- | --- | --- | --- | --- | --- |
| Equil. | 23 mM MES, 60 mM NaCl | 5.4-5.60 | 6.1-7.7 mS/cm | 13-33 mM MES 50-70 mM NaCl | 5.1-5.9 |
| Load | VF pool diluted with water for injection (WFI) | 5.3-5.7 | ≤5.5 mS/cm | ≤6.5 mS/cm | 5.2-5.8 |
| Wash 1 | 25 mM MOPS | 6.9-7.1 | 0.2-1.2 mS/cm | 15-35 mM MOPs | 6.6-7.4 |
| Wash 2 | 23 mM MES 10 mM NaCl | 5.4-5.6 | 1.2-1.8 mS/cm | 13-33 mM MES 5-20 mM NaCl | 5.1-5.9 |

TABLE 4-continued

Preferred pH, Conductivity and Molarity Ranges for Bevacizumab Process

| | Target buffer | Target pH range | Target conductivity range | Preferred buffer molarity range | Preferred buffer pH range |
|---|---|---|---|---|---|
| Elution | 23 mM MES 175 mM NaCl | 5.45-5.55 | 17.5-18.5 mS/cm | 13-33 mM MES 160-190 mM NaCl | 5.4-5.6 |
| Sanitization | 0.5N NaOH | NA | 50-60 mS/cm (1:1 diluted) | 0.5N NaCl | NA |
| Storage | 0.1N NaOH | NA | 17-27 mS/cm | 0.1N NaOH | NA |

The present process was found to be superior to the original bevacizumab process which used a first wash buffer pH 5.5. The new process herein was able to achieve pools with lower CHOP levels, it achieved a higher step yield and was an overall more robust process to run in manufacturing.

What is claimed is:

1. A method for purifying rituximab from a composition comprising the rituximab and one or more contaminants selected from the group consisting of Chinese Hamster Ovary Proteins (CHOP), leached protein A, DNA, and aggregated rituximab, which method comprises the sequential steps of:
   (a) loading the composition onto a cation exchange material wherein the composition is at a pH from about 4.0 to about 6.0;
   (b) washing the cation exchange material with a first wash buffer at a pH from about 6.8 to about 9.0 and a conductivity of 0.1 to 3 mS/cm;
   (c) washing the cation exchange material with a second wash buffer at a pH from about 5.0 to about 6.0; and
   (d) eluting the rituximab from the cation exchange material using an elution buffer with a pH from about 5.0 to about 6.0 and a conductivity from about 10 mS/cm to about 100 mS/cm.

2. The method of claim 1 wherein the elution buffer comprises about 100 to about 300 mM NaCl.

3. The method of claim 1 wherein the pH of the second wash buffer and the pH of the elution buffer are approximately the same.

4. The method of claim 1 wherein the cation exchange material comprises crosslinked poly(styrene-divinylbenzene) flow-through particles coated with a polyhydroxylated polymer functionalized with sulfopropyl groups.

5. The method of claim 1 further comprising subjecting the composition comprising rituximab to one or more further purification steps either before, during, or after steps (a) through (d) so as to obtain a homogeneous preparation of the rituximab.

6. The method of claim 5 further comprising conjugating the purified rituximab wits a heterologous molecule.

7. The method of claim 5 further comprising preparing a pharmaceutical composition by combining the homogeneous preparation of the rituximab with a pharmaceutically acceptable carrier.

8. A method for purifying bevacizumab from a composition comprising the bevacizumab and one or more contaminants selected from the group consisting of a cell culture media component, garamycin, Chinese Hamster Ovary Proteins (CHOP), DNA, viral contaminant, and aggregated bevacizumab, which method comprises the sequential steps of:
   (a) loading the composition onto a cation exchange material wherein the composition is at a pH from about 4.0 to about 6.0;
   (b) washing the cation exchange material with a first wash buffer at a pH from about 6.8 to about 8.0 and a conductivity of 0.1 to 3 mS/cm;
   (c) washing the cation exchange material with a second wash buffer at a pH from about 5.0 to about 6.0; and
   (d) eluting the bevacizumab from the cation exchange material using an elution buffer with a pH from about 5.0 to about 6.0 and a conductivity from about 10 mS/cm to about 100 mS/cm.

9. The method of claim 8 wherein the elution buffer comprises about 100 to about 300 mM NaCl.

10. The method of claim 8 wherein the pH of the second wash buffer and the pH of the elution buffer are approximately the same.

11. The method of claim 8 wherein the cation exchange material comprises crosslinked poly(styrene-divinylbenzene) flow-through particles coated with a polyhydroxylated polymer functionalized with sulfopropyl groups.

12. The method of claim 8 further comprising subjecting the composition comprising the bevacizumab to one or more further purification steps either before, during, or after steps (a) through (d) so as to obtain a homogeneous preparation of the bevacizumab.

13. The method of claim 12 further comprising conjugating the purified bevacizumab with a heterologous molecule.

14. The method of claim 12 further comprising preparing a pharmaceutical composition by combining the homogeneous preparation of the bevacizumab with a pharmaceutically acceptable carrier.

* * * * *